United States Patent [19]

Krantz et al.

[11] Patent Number: 4,602,006
[45] Date of Patent: Jul. 22, 1986

[54] YNENOLACTONE PROTEASE INHIBITORS

[75] Inventors: Alexander Krantz, Toronto; Tim F. Tam; Robin W. Spencer, both of Mississauga, all of Canada

[73] Assignee: Syntex (U.S.A.) Inc., Palo Alto, Calif.

[21] Appl. No.: 608,340

[22] Filed: May 9, 1984

[51] Int. Cl.[4] .................. C07D 307/58; C07F 7/08; A61K 31/695; A61K 31/365
[52] U.S. Cl. ..................... 514/63; 514/473; 549/214; 549/295; 549/273
[58] Field of Search ............... 549/295, 214, 273, 323, 549/324; 424/279; 514/63, 473

[56] References Cited

U.S. PATENT DOCUMENTS 3,770,776  11/1973  Collins et al. .................. 549/422

OTHER PUBLICATIONS

Chemical Abstracts, 92:181374t (1980).
Chemical Abstracts, 95:198981y (1981).
Daniels et al., J. Biol. Chem., vol. 258, No. 24, pp. 15046-15053 (1983).
Bohlmann and Zdero, 102 Chem. Ber. 1034-1036 (1969).
Wat et al., vol. 9, No. 1, Biochemical Systematics and Ecology, pp. 59-62 (1981).
Bohlmann and Jakupovic, vol. 18, No. 8, Phytochemistry, pp. 1367-1370 (1979).
Sofia et al., 48 J. Org. Chem. 3318-3325 (1983).
Chakravarty et al., vol. 257, No. 2, Journal of Biological Chemistry, pp. 610-612 (1982).
Krafft et al., vol. 103, No. 18, J. Am. Chem. Soc., 5459-5466.

Primary Examiner—Norma S. Milestone
Attorney, Agent, or Firm—Liza K. Toth; Tom M. Moran

[57] ABSTRACT

Compounds of the formula

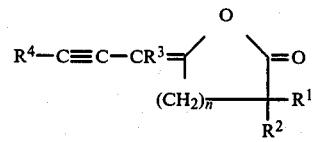

wherein n is 1-3; $R^1$, $R^2$ and $R^3$ are the same or different and are hydrogen, lower alkyl, lower alkenyl, lower alkynyl, aryl or aryl lower alkyl wherein when aryl is phenyl it is unsubstituted or independently substituted with one or more halo, lower alkyl or lower alkoxy groups; and $R^4$ is hydrogen, lower alkyl, lower alkenyl, lower alkynyl, trialkylsilyl, aryl or aryl lower alkyl wherein when aryl is phenyl it is unsubstituted or independently substituted by one or more halo, lower alkyl or lower alkoxy groups; excluding those compounds wherein $R^1$ and $R^2$ are hydrogen and $R^4$ is ethyl, propyl or butyl. These compounds are useful as protease inhibitors.

8 Claims, No Drawings

YNENOLACTONE PROTEASE INHIBITORS

BACKGROUND OF THE INVENTION

This invention relates to certain lactones which contain a conjugated triple and double bond functionality. More specifically, this invention relates to certain lactones which have a conjugated triple and double bond with the double bond linked directly to the ether oxygen of the lactone. These compounds are useful as protease inhibitors.

The lactones of this invention are represented by formula I.

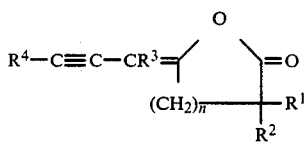

wherein n is 1-3; $R^1$, $R^2$ and $R^3$ are the same or different and are hydrogen, lower alkyl, lower alkenyl, lower alkynyl, aryl, or aryl lower alkyl wherein when aryl is phenyl it is unsubstituted or independently substituted with one or more halo, lower alkyl or lower alkoxy groups; and $R^4$ is hydrogen, lower alkyl, lower alkenyl, lower alkynyl, trialkylsilyl, aryl or aryl lower alkyl wherein when aryl is phenyl it is unsubstituted or independently substituted by one or more halo, lower alkyl or lower alkoxy groups, excluding those compounds wherein $R^1$ and $R^2$ are hydrogen and $R^4$ is ethyl, propyl or butyl.

Derivatives of 5(E)-(2-iodoalkylidene)-tetrahydro-2-furanone compounds have been used as mechanism-based inhibitors for certain proteases. The synthesis and biological activity of these compounds have been reported by Krafft, G. A. and Katzenellenbogen, J. A., *J. Am. Chem. Soc.*, 103, 5459 (1981); Chakravarty, P. K., et al., *J. Biol. Chem.*, 257, 610 (1982); Sofia, M. J., et al., *J. Org. Chem.*, 48, 3318 (1983); and Daniels S. B., et al., *J. Biol. Chem.*, 258, 15046 (1983). See also the compounds disclosed in Chemical Abstracts 95:198981y, 92:181374t, and 70:93914j.

The subject compounds of this invention are enzyme inhibitors, particularly of proteolytic enzymes including endopeptidases and exopeptidases. Protease inhibitors may be useful in the treatment of a number of diseases including pulmonary emphysema, [Janoff, A., Chest 83 54–58 (1983)] and adult respiratory distress syndrome [Hopewell, P. C. and Murray, J. F. *Ann. Rev. Med.* 27, 343 (1976)] in which elastase has been implicated; in inflammation in which elastase, collagenase and other lysosomal hydrolases have been implicated; in tumor cell metastasis (in which plasminogen activator, human leukocyte elastase, cathepsin B and related enzymes are thought to play an important role in the pathology [Salo, et al., *Int. J. Cancer*, 30, 669–673, (1973); Kao, et al., *Biochem. Biophys. Res. Comm.*, 105, 383–389, (1982); Powers, J. C., in "Modification of Proteins," R. E. Feeney and J. R. Whitaker, Eds., Adv. Chem. Ser., 198, Amer. Chem. Soc., Wash., D.C., pp. 347-367, (1982)]; for the treatment of hypertension (angiotensin converting enzyme), (Ondetti, M. A., et al., Science, 196, 441 (1977), in various blood diseases involving venous and arterial thromboembolic disorders [O'Reilly, R. A., in "The Pharmacological Basis of Therapeutics", 6th Edt., Goodman, A. G., Goodman, L. S., Gilman, A., Eds., (1980)]; and in the control of conception, [Zaneveld, L. J. D., et al., *Biol. Repro.* 20, 1045 (1979)], support a role for acrosin inhibitors as contraceptives.

In addition, this invention relates to a pharmaceutically acceptable formulation comprising at least one compound of formula I in admixture with a pharmaceutically acceptable excipient.

In yet another aspect, this invention relates to a method for inhibiting protease activity which method comprises administering to a mammal a therapeutically effective amount of a compound of formula I either alone or with a pharmaceutically acceptable excipient.

Another aspect of this invention relates to a process for preparing compounds of formula I which comprises treating a terminal alkyne derivative with a compound of formula 2

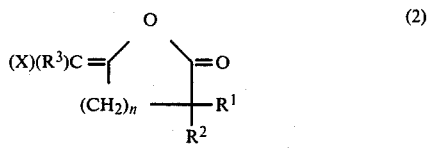

wherein X is iodo, bromo and chloro and n, $R^1$, $R^2$ and $R^3$ are defined herein about to form a compound of formula I wherein $R^4$ is not hydrogen; or treating with silver nitrate and an alkali metal cyanide a compound of formula (3)

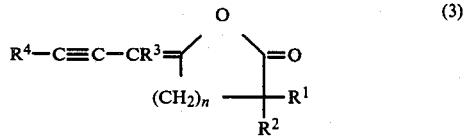

wherein n, $R^1$, $R^2$ and $R^3$ are defined hereinabove and $R^4$ is trialkylsilyl to give a compound of formula I wherein $R^4$ is hydrogen.

The preferred compounds of the invention are those wherein n is 1 or 2 and $R^1$, $R^2$, and $R^3$ are independently hydrogen, lower alkyl, phenyl, phenyl lower alkyl wherein phenyl is unsubstituted or independently substituted with one or more halo, lower alkyl or lower alkoxy groups and $R^4$ is trialkylsilyl, hydrogen, lower alkyl, phenyl, or phenyl lower alkyl.

More preferred are those compounds wherein n is 1 or 2 and $R^1$ is hydrogen or lower alkyl, $R^2$ is hydrogen, lower alkyl, phenyl, or phenyl lower alkyl; $R^3$ is hydrogen or lower alkyl; and $R^4$ is trialkylsilyl, hydrogen or lower alkyl.

The most preferred are:
3-benzyl-5(E)-(prop-2-ynylidene)tetrahydro-2-furanone;
3-n-butyl-5(E)-(prop-2-ynylidene)tetrahydro-2-furanone;
3-methyl-3-benzyl-5(E)-(prop-2-ynylidene)tetrahydro-2-furanone;
3-isopropyl-3-benzyl-5(E)-(prop-2-ynylidene)tetrahydro-2-furanone;
3-benzyl-5(E)-(3-methylprop-2-ynylidene)tetrahydro-2-furanone; and
3-benzyl-5(E)-(prop-2-ynylidene)tetrahydro-2-pyrone.

For the purposes of this invention the term "lower alkyl" means a radical of 1-6 carbon atoms, either straight or branched, as exemplified by methyl, ethyl, propyl, isopropyl, n-butyl, t-butyl, isobutyl, pentyl, hexyl, and the like. Alkyl as used herein has the same meaning as lower alkyl.

Lower alkoxy is an alkoxy group of 1–6 carbon atoms as referred to hereinabove as a lower alkyl radical and is exemplified by methoxy, ethoxy, propoxy, butoxy, and the like.

Lower alkenyl refers to a radical of 2–6 carbon atoms which has one or more double bonds.

The term lower alkynyl refers to a radical of 2–6 carbon atoms having at least one triple bond.

Aryl is an aromatic group which may be phenyl, naphthyl, thiophenyl, furanyl, and the like. Aryl lower alkyl means a radical having an aromatic group substituted on a lower alkyl radical, the lower alkyl radical serving as the bridge between the aromatic group and the remainder of the molecule wherein aryl has the definition given above.

Halo refers to fluoro, chloro, bromo, and iodo.

A pharmaceutically acceptable composition is one safe for use in humans and comprising at least one pharmaceutically acceptable excipient and an amount of a compound of formula I which is not toxic, preferably a therapeutically effective amount.

Administration of the active compounds described herein can be via any of the accepted modes of administration for agents which are systemically active. These methods include oral, parenteral, and otherwise systemic or aerosol forms, including delayed release, implantable formulations.

Depending on the intended mode of administration, the compositions may be in the form of solid, semi-solid, or liquid dosage forms, such as, for example, tablets, suppositories, pills, capsules, powders, liquids, suspensions, or the like, preferably in unidose forms suitable for single administration of precise dosages. The compositions of this type will include a conventional pharmaceutical carrier or excipient and an active compound of formula I. Such formulations may additionally include other medicinal agents, pharmaceutical agents, carriers, or the like.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795.

For systemic administration via suppository, traditional binders and carriers include, e.g. polyalkylene glycols or triglycerides. Such suppositories may be formed from mixtures containing active ingredient in the range of 0.5%–10%; preferably 1–2%.

For aerosol administration, the active ingredient is preferably supplied in finely divided form along with a surfactant and a propellant. Typical percentages of active ingredients are 0.01 to 20% by weight, preferably 0.04 to 1.0%.

The protease inhibition activity of those compounds may be determined by the methods of Krafft, G. A. and Katzenellenbogen, J. A., *J. Am. Chem. Soc.*, 103, 5459 (1981) or any of the other publications set out herein above on page 2.

These compounds will exhibit stereoisomerism when $R^1$ and $R^2$ are different. It is to be understood that the representation of formula I provided herein encompasses all stereoisomers whether existing as a racemic mixture or separated into their individual isomers. In this discussion, the racemic mixture will be refered to where appropriate, unless otherwise indicated.

In addition, the compounds of this invention may exist as geometric isomers as represented by formula A and formula B.

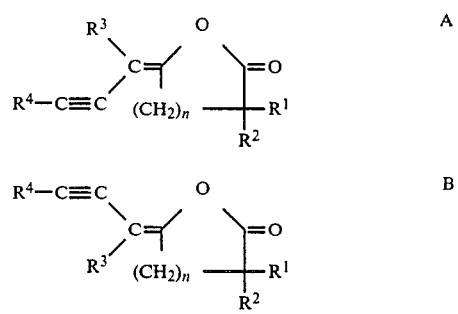

Synthesis of the ynenolactone affords primarily the A structure and a minor amount of B.

The geometry of formula A may be altered by UV irradiation the manner of Hammond, G. S., et al., *J. Am. Chem. Soc.*, 86, 3197 (1964), to obtain a photostationary state between formula A and its geometric isomer formula B. Further, E-haloenol lactones of the formula

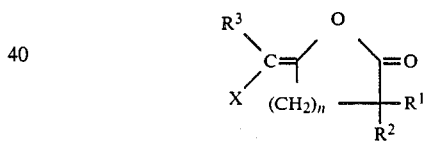

can be isomerized by exposure to acid or silica gel for prolonged periods (Krafft, G. A., and Katzenellenbogen, J. A. *J. Am. Chem. Soc.*, 103, 5459 (1981); the Z-haloenol lactones can then be converted to Z-ynenolactones in the fashion indicated above for the corresponding E forms. Formula I as written herein encompasses both isomers whether present as mixtures or as the individual isomer.

SPECIFIC EMBODIMENTS

These compounds are conveniently made by first preparing an alkynoic acid derivative wherein the alpha-carbon is substituted with $R^1$ and $R^2$ and having a triple bond at position 4 or 5 and the $R^3$ group comprising the remainder of the acid. This compound is then treated with N-iodosuccinimide in the presence of a weak base and a catalytic amount of tetrabutylammonium hydroxide to form the iodomethylidene-lactone derivative. The resulting compound is then reacted with an alkyne derivative to give the compounds of formula I.

The alkynoic acids required to make the compounds of formula I wherein n is 2 are prepared by the methods graphically outlined in Reaction Scheme I.

REACTION SCHEME IA

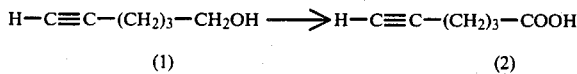

REACTION SCHEME IB

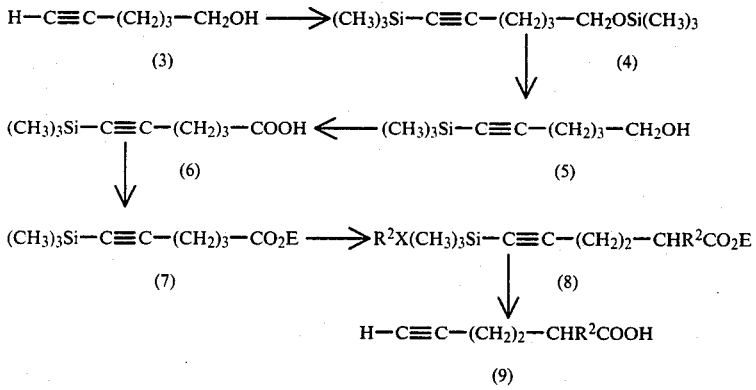

In the preceding Reaction Scheme, E is a lower alkyl radical which forms an ester group. $R^2$ is the same as defined hereinabove. While the silyl group in formulas 4–8 are illustrated as being trimethyl, any other appropriate trialkylsilyl blocking group such as t-butyldimethylsilyl or the like, could be used instead.

The 5-hexynoic acid of Scheme IA may be prepared by the method of Holland, B. C. and N. W. Gillman, Syn. Comm., (4), 203 (1974). Alternatively, 5-hexynoic acid can be prepared by oxidation of 5-hexanol with a chromate oxidant such as pyridinium dichromate in dimethylformamide and the like.

Preparation of the alkynoic acid needed to make the compounds of formula I wherein n is 2 and $R^2$ is not hydrogen is carried by the sequence illustrated Scheme IB. The 5-hexynol is commercially available. Preparation of compound 4 is carried out by treating the alcohol with an excess of n-butyl lithium and a trialkyl silyl halide (at least 2 equivalents) in an inert organic solvent under an inert atmosphere at reduced temperature. Preferably the reaction will be carried out in a solvent such as tetrahydrofuran under an inert atmosphere such as argon. The n-butyl lithium is added to a solution of the alcohol pre-cooled to approximately −40° C. When addition of the n-butyl lithium is completed, the reaction solution is warmed to approximately −20° C. and the silylating agent, preferably trimethylsilyl chloride, is added slowly. The reaction is then completed by allowing the solution to stand at room temperature overnight.

The alcohol of formula 5 is obtained by treating the crude product obtained from the silylation reaction with a concentrated mineral acid in the presence of a polar solvent such as an alcohol. Preferably an aqueous alcohol/concentrated hydrochloric acid will be used to effect this hydrolysis. The reaction is effected at room temperature in about one hour. The product is recovered by conventional means.

The alcohol of formula 5 is then treated with a mild oxidizing agent, particularly a chromium-based oxidant. A number of chromate oxidizing agents are known in the art and may be used to effect this reaction. Herein it is preferred to use pyridinium dichromate in the presence of dry dimethylformamide to effect the oxidation. The reaction is preferably carried out in the dark over about 24 hours after which the product, formula 6, is recovered by conventional means.

Introduction of the $R^2$ group onto the alpha-carbon of formula 7 necessitates converting the acid to an ester. This is accomplished by treating the acid with 1,1-carbonyldiimidazole in a dry solvent under an inert atmosphere and then adding the appropriate alkanol in the presence of a catalytic amount of pyridine. The reaction is most conveniently effected by forming a solution of the 1,1-carbonyldiimidazole in dry tetrahydrofuran under nitrogen, adding the acid in the same solvents, then adding the alkanol, preferably ethanol with a small amount of pyridine. The resulting mixture is stirred at room temperature for several days, preferably 48 hours. The product is recovered by conventional means.

Compounds of formula 8 are made by treating the alkyl ester of formula 7 with the appropriate $R^2$-halide in the presence of a strong base, such as n-butyl lithium and a dialkylamine. The reaction is carried out in a dry solvent under an inert atmosphere, for example, dry tetrahydrofuran under argon. The n-butyl lithium is added to a solution of dialkylamine, preferably diisopropylamine, at a reduced temperature (−10° to +10° C.). After stirring for a short period, the solution is cooled to about −78° C. after which the ester of formula 7 is added slowly in the same solvent. After the reagents are well-mixed, a solution of $R^2X$ (X is halo) in dry solvent is added and the reaction mixture allowed to warm to room temperature. A crude product is recovered by conventional means.

Crude ester of formula 8 is then treated with a dilute solution of a strong base such as sodium hydroxide, potassium hydroxide, or the like, in an alcohol such as ethanol. The mixture is refluxed for several hours, preferably about 1.5, and then left at room temperature overnight. The product of formula 9 is recovered and purified by conventional means.

The alkynoic acids needed to make those compounds of formula I wherein is n is 1 and $R^1$ is hydrogen may be made by the reaction sequences set out in Reaction Scheme II.

REACTION SCHEME II

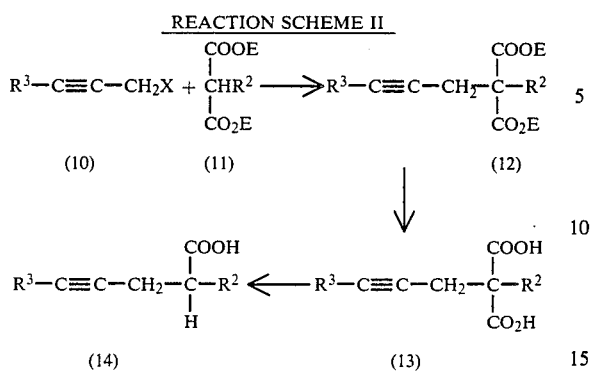

$R^2$ and $R^3$ in the foregoing Scheme are defined hereinabove. E is an ester-forming group, preferably lower alkyl. X is halo, preferably bromo.

The malonate derivatives represented by formula 11 are alkylated by the propargyl halo derivatives of formula 10. A number of malonate derivatives and propargyl halo derivatives are available commercially or can be made by published procedures. See for example L. Brandsma and H. D. Verkruijsse, "Synthesis of Acetylene, Allene, and Cumulenes", p. 221, Elsevier Scientific Publishing Co., New York (1981); L. Brandsma, "Preparative Acetylene Chemistry," p. 158, Elsevier Publishing Co.; R. B. Miller, Synthetic Commun., 2, 287, (1972); J. Cologne and R. Gelin, *Memoires Presentes A La Societe Chimique,* 797 (1954). The alkylation is effected by first dissolving an alkali metal in an alcohol, preferably sodium and ethanol, then adding to this solution the malonate derivative followed by the propargyl halide derivative. The metal alkoxide solution is formed at about 0° C. The malonate derivative and propargyl halide derivative are added at this temperature (about 0° C.) after which the reaction mixture is refluxed for 2 to 6 hours, preferably about 4 hours, to effect the alkylation.

Ester hydrolysis is effected by means of a dilute solution of a strong base, the reaction being carried out in an appropriate solvent such as an alcohol. Preferably the base will be sodium hydroxide and preferably will be carried out in a solvent comprising 1 part water to 9 parts alcohol. The hydrolysis is effected by refluxing the reaction mixture overnight or for whatever time period is necessary to effect the hydrolysis.

To make the compounds of formula 14, the diacid of formula 13 is subjected to heat in order to effect thermal loss of carbon dioxide. A neat solution of the diacid is heated at an appropriate elevated temperature in a distillation apparatus while monitoring gas evolution. Heating is terminated when gas evolution ceases or after about an hour, usually about 30–45 minutes.

The compounds of formula I wherein $R^1$ and $R^2$ are both something other than hydrogen are most conveniently prepared by the method outlined in Reaction Scheme III.

REACTION SCHEME III

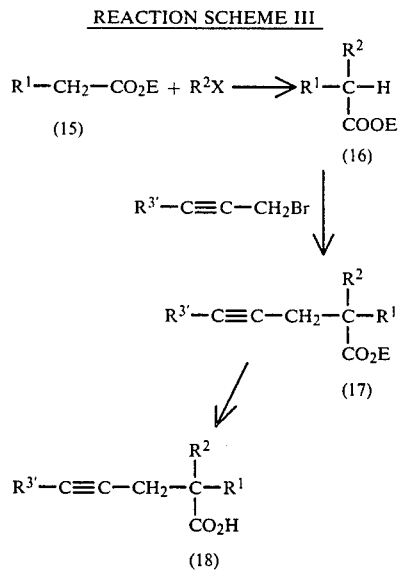

In this Reaction Scheme X is halo, $R^1$ and $R^2$ are the same as defined hereinabove, $R^{3'}$ is trialkylsilyl or $R^3$ as defined herein above and E is lower alkyl.

Alkylation of the acid ester represented by formula 15 is carried out as described hereinabove for the conversion of formula 7 to formula 8. The reaction of formula 16 with the illustrated propargyl halide derivative is effected in the same manner as described hereinabove for reacting formula 10 with formula 11 to make formula 12. The resulting ester, formula 17, is hydrolyzed to give formula 18 using base as is described hereinabove for the hydrolysis of formula 7 to give the acid of formula 8.

The final several steps for making formula I compounds comprise treating an alkanoic acid derivative prepared in Reaction Schemes I, II or III with N-iodosuccinimide and a weak base in the presence of a catalytic amount of tetra-n-butylammonium hydroxide. This gives the iodomethylidene-lactone derivatives of formula 19 (Reaction Scheme IV). These compounds are then reacted with an alkyne derivative by one of three different methods to give the compounds of formula I. The compounds of formula I wherein $R^4$ is trialkylsilyl are treated with a hydrolytic agent to remove the trialkylsilyl moiety, giving a compound wherein $R^4$ is hydrogen. Reaction Scheme IV is as follows.

REACTION SCHEME IV

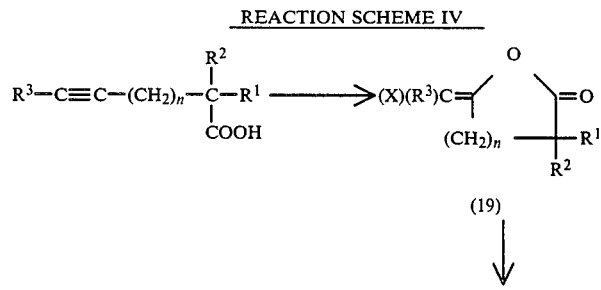

REACTION SCHEME IV

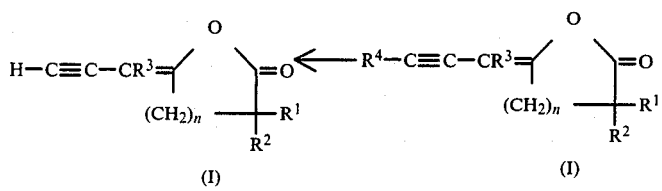

The definition of $R^1$, $R^2$, $R^3$ and $R^4$ here are the same as recited hereinabove.

Formation of the iodomethylidene-lactone structure is effected by treating the alkynoic acid with a slight excess of N-iodosuccinimide, a slight excess of a weak base such as sodium bicarbonate, and a catalytic amount of tetra-n-butylammonium hydroxide (approximately 0.1 to 0.2 equivalents) in an appropriate organic solvent such as methylene chloride, or the like. The reaction is stirred for 15 to 60 minutes, preferably 30 minutes, after which the product is recovered by conventional means.

Compounds of Formula 19 are converted to those of formula I by three methods. In one, a cuprous alkyne derivative is used. This reaction follows the conditions of Atkinson, R. E., et al., *Chemistry and Industry*, 2101, (1964) or Atkinson, E. E., et al., *J. Chem. Soc.* (C), 1578 (1967). This reaction is carried out in a solvent such as dimethylformamide or pyridine under an inert atmosphere such as argon. Usually the reaction mixture is heated to about 80°–150° C., preferably about 110° C. for about 1½ days in order to effect the reaction.

An alternative is to effect a palladium-copper coupling reaction between an alkyne derivative and the iodoalkylidene-lactone using the conditions of, for example, Ando, T., et al., *Agri. C. Biol. Chem.*, 46, (3), 717 (1982) or Robbins, M. and P. J. Barr, *Tetrahedron Letters*, 421 (1981).

A third method is one wherein compound 20 is reacted with an alkyne derivative in the presence of a catalytic amount of palladium acetate and triphenylphosphine in a refluxing solvent. This reaction follows the conditions of Austin, W. B., et al., *J. Org. Chem.*, 46, 2280 (1981).

When conversion of compounds of formula 20 to those of formula I result in $R^4$ group which is trialkylsilyl, such compounds may be converted to their hydrogen analog ($R^4$ equals hydrogen) by treatment with silver nitrate and potassium cyanide following the method of Ahmed, M., et al., *J. Chem. Soc., Perkin, I.*, 1981 (1974) or Schmidt, H. M. and J. A. Arens, *Rec. Tran. Chim.*, 86, 1138 (1967).

PREPARATION I

5-Hexynoic acid

To a solution of 138 gm pyridinium dichromate in 2 ml of dry dimethylformamide, was added 6 gm of 5-hexynol. The solution was stirred in the dark for 16 hours and diluted with 1 liter of ether. The dark residue was recovered by suction filtration through a pad of Celite. The filtrate was passed through a Fluorosil ® column eluted with ether. The combined ethereal wash was evaporated to an oil. The dimethylformamide was removed by distillation under reduced pressure. The residual oil was then vacuum distilled, b.p. 77°–80° C. (1 mm Hg).

PREPARATION II

6-Trimethylsilylhex-5-ynol

To a 3-neck flask equipped with a 500 ml pressure equalizing funnel and an argon gas inlet/outlet, was added 50 gm of 5 hexynol in 100 ml of tetrahydrofuran under argon. The flask and its contents were flushed with argon, and then n-butyllithium (70 ml, 1.6M) was added dropwise over a period of 45 min. at −40° C. A white precipitate started to form after approximately 30 min. The solution was then warmed to −20° C. and 130 ml of trimethylsilyl chloride was added dropwise over a 30 min. period. The reaction mixture was left at room temperature overnight.

The mixture was filtered and the filtrate evaporated to an oil. The oily residue was partitioned between ether and saturated ammonium chloride solution. The ether layer was washed with water and dried over magnesium sulphate and then evaporated to give an oil.

To this oil, was added 80 ml of ethanol, 0.5 ml of concentrated hydrochloric acid and 5 ml of water. The mixture was stirred at room temperature for 1 hour. Saturated brine solution was added and the mixture was extracted with ether. The combined ethereal extracts were further washed with water and dried over magnesium sulphate. Solvent evaporation gave an oil which was distilled to give the title compound, b.p. 80° C., (0.1 mm Hg); IR: 3300–3400, 2160, 1250 cm$^{-1}$.

PREPARATION III

6-Trimethylsilylhex-5-ynoic Acid

To a solution of 10 gm of 6-trimethylsilylhex-5-ynol in 400 ml of dry dimethylformamide, was added 98 gm of pyridinium dichromate. The solution was stirred in the dark for 24 hours and then partitioned between ether and water. The ether extract was dried over magnesium sulphate and evaporated to an oil. Distillation gave the title compound, b.p. 121°–124° C. (1 mm Hg), IR: 3290, 2162, 1720 cm$^{-1}$.

PREPARATION IV

Ethyl 6-trimethylsilylhex-5-ynoate

To a solution of 5.3 gm of 1,1-carbonyldiimidazole in 80 ml of dry tetrahydrofuran under argon, was added a solution of 5.03 gm of 6-trimethylsilyl-5-hexynoic acid in 15 ml of dry tetrahydrofuran. The mixture was stirred for 1 hour. Absolute ethanol (80 ml) and pyridine (1 ml) were then added, and the resulting mixture was stirred at room temperature for 48 hours. The solvent was evaporated and the residual oil was extracted with ether and 1.5% hydrochloric acid. The ethereal layer, which was washed with water and then dried, was evaporated to an oil. This material was purified by distillation, b.p. 70°–75° C. (0.6 mm Hg); IR: 2170, 1735 cm$^{-1}$.

PREPARATION V

2-Benzylhex-5-ynoic Acid

To a 3-neck-flask equipped with septum and inert gas inlet and outlet, was added 15 ml of dry tetrahydrofuran and 1.6 ml of diisopropylamine. The flask and its contents were flushed with argon. n-Butyllithium (7 ml, 1.6M) was added at 0° C. and the resulting solution was stirred at 0° C. for 30 min. The solution was cooled to −78° C. A solution of ethyl 6-trimethylsilylhex-5-ynoate in dry tetrahydrofuran was added slowly. The resulting mixture was then stirred for 25 min. A solution of benzyl bromide in dry tetrahydrofuran was added and the reaction mixture was allowed to warm up to room temperature slowly. After standing for two days, the solvent was evaporated, and the residue was partitioned between ether and 5% hydrochloric acid. The ethereal extract, which was washed with water and dried, was evaporated to an oil.

Sodium hydroxide (5%, 35 ml) and ethanol (60 ml) were added to this oil. The mixture was refluxed for 75 min. and then left at room temperature overnight. Ethanol was removed under reduced pressure. The residue was partitioned between ether and 5% hydrochloric acid. The ethereal layer was washed with 5% sodium hydroxide solution (2×75 ml). The basic extract was acidified to pH 1 with dropwise addition of concentrated hydrochloric acid. The acidified solution was extracted with ether. The ethereal extract, which was washed with water and dried, was evaporated to an oil. This oil was recrystallized from ether/hexane, m.p. 125°–126° C.; IR: 3290, 2110, 1770 cm$^{-1}$.

PREPARATION VI

Ethyl 2-Methyl-3-phenylpropionate

A 3-neck flask was equipped with argon gas inlet and outlet, and a septum. The flask was charged with argon. A solution of 6.8 gm of diisopropylamine in 40 ml of dry tetrahydrofuran was injected into the flask. n-Butyllithium (42.2 ml, 1.6M) was added slowly at 0° C. The resulting mixture was stirred at 0° C. for 30 min. and then cooled to −78° C. A solution of ethyl 3-phenylpropionate was added slowly. Following the addition, the solution was stirred at −78° C. for 30 min. A solution of methyl iodide (10 gm) in 5 ml of dry tetrahydrofuran was then added. The mixture was stirred at −78° C. for 1 hour and then warmed to room temperature for 1 hour. The solution was partitioned between ether and water. The ethereal layer, was washed with 5% hydrochloric acid, brine solution and water, was dried over magnesium sulfate and evaporated to give an oil. The material was purified by distillation, b.p. 80°–85° C. (0.6 mm Hg); IR: 3100–2800, 1732 cm$^{-1}$.

In a similar manner, but replacing ethyl 3-phenyl propionate with ethyl propionate, and replacing methyl iodide with benzyl bromide, ethyl 2-methyl-3-phenylpropionate was prepared (b.p. 80°–85° C., 0.6 mm Hg).

PREPARATION VII

Ethyl 2-Benzyl-2-methyl-5-trimethylsilylpent-4-ynoate

To a solution of 2.2 ml (1.58 gm) of diisopropylamine in 20 ml of dry tetrahydrofuran, was added dropwise a solution of n-butyllithium (9.7 ml, 1.6M) at 0° C. The solution was stirred at 0° C. for 30 min, then cooled to −78° C. A solution of 2.5 gm of ethyl 3-phenyl-2-methylpropionate in 10 ml of dry tetrahydrofuran was added. After 30 min., 3 gm of trimethylsilylpropargyl bromide in 10 ml dry tetrahydrofuran was added. The mixture was warmed up to 0° C. slowly and maintained at 0° C. for 1.75 hours. The reaction mixture was quenched with 5% hydrochloric acid and partitioned between ether and 5% hydrochloric acid. The ethereal layer, washed with brine solution and water was dried and evaporated in an oil. The oil was chromatographed on silica gel (5% ethyl acetate; petroleum ether). This procedure yielded the title compound, IR: 2170, 1738 cm$^{-1}$.

Proceeding similarly, but replacing ethyl 2-methyl-3-phenylpropionate with ethyl 3-methylbutanoate, ethyl 2-isopropyl-5-trimethylsilylpent-4-ynoate was prepared, b.p. 84°–85° C. (1 mm Hg).

Also, by replacing ethyl 2-methyl-3-phenylpropionate with ethyl 3-phenylpropionate and replacing trimethylsilylpropargyl bromide with 1-bromo-2-butyne, ethyl 2-benzyl-4-hexynoate was prepared; m.p. 91°–93° C.; IR: 3100–2800, 1740 cm$^{-1}$.

PREPARATION VIII

2-Benzyl-2-methylpent-4-ynoic Acid

To a solution of 2.65 gm of ethyl 2-benzyl-2-methyl-5-trimethylsilylpent-4-ynoate in 20 ml ethanol, was added 30 ml of 5% sodium hydroxide solution. The mixture was refluxed overnight at which time the ethanol was removed under reduced pressure. The solution was acidified by dropwise addition of concentrated hydrochloric acid and extracted with ether. The ethereal extract was washed with 5% sodium hydroxide solution. The basic wash was acidified with concentrated hydrochloric acid and extracted with ether. The ethereal extract, washed with water and dried, was evaporated to an oily solid. This oily material was chromatograhed on silica gel (5% ethyl acetate in petroleum ether). The product was recrystallized from petroleum ether (30–60); m.p. 87.5°–91.5° C.; IR: 3300, 2112, 1690 cm$^{-1}$.

By replacing ethyl 2-benzyl-2-methyl-5-trimethylsilylpent-4-ynoate with ethyl 2-isopropyl-5-trimethylsilyl-4-pentynoate, 2-isopropyl-4-pentynoic acid was prepared; b.p. 95°–96° C. (1 mm Hg); IR: 3300, 1700, 2500–3500 (br) cm$^{-1}$.

By replacing ethyl 2-benzyl-2-methyl-5-trimethylsilylpent-4-ynoate with ethyl 2-benzylhex-4-ynoate, 2-benzylhex-4-ynoic acid was prepared; IR: 3300–2500, 1710 cm$^{-1}$.

PREPARATION IX

Ethyl 2-Carboethoxy-2-propargylhexanoate

Clean sodium (1.2 gm) was cut into small pieces and added in small portions to 125 ml of absolute ethanol at 0° C. The reaction mixture was stirred for 1 hour at which time all sodium had dissolved. Diethyl n-butylmalonate (10 gm) was added. After 10 min., propargyl bromide (6.5 ml) was added. The reaction mixture was refluxed for 4 hours and then evaporated to dryness. The residue was partitioned between ether and 10% hydrochloric acid. The ethereal layer, which was washed with water and dried, then was evaporated to an oil. The crude product was further purified by distillation, b.p. 104°–106° C.

Proceeding similarly, but replacing diethyl n-butylmalonate with diethyl benzylmalonate, ethyl 2-benzyl-2-carboethoxypent-4-ynoate was prepared. Also by replacing diethyl n-butylmalonate with diethyl benzylmalonate, replacing propargyl bromide with 1-bromo- 2-butyne, ethyl 2-benzyl-2-carboethoxyhex-4-ynoate was prepared.

PREPARATION X 2-Propargylhexanoic Acid

A solution of 8.2 gm of ethyl 2-carboethoxy-2-propargylhexanoate in 100 ml of 6% potassium hydroxide (90 ml ethanol:10 ml water) was refluxed for 4 hours. Ethanol was removed under reduced pressure. The residue was acidified with 10% hydrochloric acid and extracted with ether. The ethereal extract, washed with water and dried, was evaporated to an oil. The oil was pumped under high vacuum overnight.

This oil was heated to 150° C. in a distillation apparatus for 30 min. Gas evolution was monitored by a bubbler. The acid was cooled and then partitioned between 6% potassium hydroxide and ether. The basic extract was acidified to pH 1 with dropwise addition of concentrated hydrochloric acid. The acidified fraction was extracted with ether. The ethereal layer was washed with brine solution, water and then dried. Evaporation of the solvent gave an oil which was chromatographed on silica gel (elution gradient: 20% ethyl acetate:hexane to 40% ethyl acetate:hexane) and further purified by distillation, b.p. 110°–112° C. (1 mm Hg).

By replacing ethyl 2-carboethoxy-2-propargylhexanoate with ethyl 2-benzyl-2-carboethoxypent-4-ynoate, 2-benzylpent-4-ynoic acid was prepared, IR: 3290, 1710 cm$^{-1}$.

Proceeding similarly, but replacing ethyl 2-carboethoxy-2-propargylhexanoate with ethyl 2-benzyl-2-carboethoxy-4-hexynoate, 2-benzyl-4-hexynoic acid is prepared.

EXAMPLE 1

5(E)-Iodomethylidenetetrahydro-2-furanone

To a solution of 4-pentynoic acid (1.08 gm) in 25 ml methylene chloride, was added sequentially, N-iodosuccinimide (2.76 gm), sodium bicarbonate (1.03 gm) and 2 ml of tetra-butylammonium hydroxide (40% in water). The reaction mixture was stirred vigorously for 30 min and then diluted with 50 ml of methylene chloride The resulting mixture was extracted with 5% sodium thiosulphate solution, brine solution and water. The methylene chloride layer, dried over sodium sulphate, was evaporated to an oil. This oil was further purified by flash column chromatography (silica gel 60, 10% ethyl acetate and petroleum ether), IR: 1810, 1655 cm$^{-1}$.

Similarly, but replacing 4-pentynoic acid with the acids of Preparation VIII and X, the following compounds were prepared:
3-benzyl-3-methyl-5(E)-iodomethylidenetetrahydro-2-furanone, m.p. 75°–78° C.; IR: 1788, 1657 cm$^{-1}$.
3-benzyl-5(E)-iodomethylidenetetrahydro-2-furanone, oil; IR: 3020, 3080, 1800, 1655 cm$^{-1}$;
3-butyl-5(E)-iodomethylidenetetrahydro-2-furanone, oil; IR: 3080, 1800, 1655 cm$^{-1}$;
3-isopropyl-5(E)-iodomethylidenetetrahydro-2-furanone; IR: 1800, 1650 cm$^{-1}$; and
3-benzyl-5(E)-iodoethylidenetetrahydro-2-furanone. MS: 328 (M+).

By replacing 4-pentynoic acid with the acids of Preparations I or V, the following compounds were prepared:
6(E)-iodomethylidenetetrahydro-2-pyrone, IR: 1750, 1610, cm$^{-1}$; and
3-benzyl-6(E)-iodomethylidenetetrahydro-2-pyrone, IR: 1750, 1620, cm$^{-1}$.

EXAMPLE 2

5(E)-(3-Phenylprop-2-ynylidene)tetrahydro-2-furanone

A mixture of cuprous phenylacetylide (0.65 gm) and 5(E)-iodomethylidenetetrahydro-2-furanone (0.809 gm) in 20 ml of dry diethylformamide was heated at 110° C. for 1½ days under argon. The solution was cooled, and partitioned between ether and water. The ether layer, dried over magnesium sulphate, and then evaporated to an oil. The oil was purified by repeated column chromatography on silica gel (elution gradient, 10% ethyl acetate:petroleum ether to 20% ethyl acetate:petroleum ether; R$_f$ of product —0.5 at 20% ethyl acetate:petroleum ether). This gave the title product 5(E)-(3-phenylprop-2-ynylidene)tetrahydro-2-furanone, m.p. 90°–91° C.; IR: 1810, 1655 cm$^{-1}$.

Proceeding in a similar manner but replacing 5(E)-iodomethylidenetetrahydro-2-furanone with 6(E)-iodomethylidenehexahydro-2-pyrone, 6(E)-(3-phenyl-2-propynylidene)tetrahydro-b 2-pyrone was prepared, m.p. 79°–80° C.; IR: 1760, 1640 cm$^{-1}$.

Also by replacing cuprous phenylacetylide with cuprous heptyne, 5(E)-(2-heptynylidene)tetrahydro-2-furanone was prepared, oil, IR: 1815, 1665 cm$^{-1}$.

By replacing cuprous phenylacetylide with cuprous heptyne and replacing 5(E)-iodomethylidenetetrahydro-2-furanone with 6(E)-iodomethylidenetetrahydro-2-pyrone, 6(E)-(2-heptynylidene)hexahydro-2-pyrone was prepared, oil; IR: 1760, 1640 cm$^{-1}$.

EXAMPLE 3

5(E)-(3-Trimethylsilylprop-2-ynylidene)-tetrahydro-2-furanone

To a solution of 5(E)-iodomethylidenetetrahydro-2-furanone (820 mg), palladium (II) acetate (40 mg) and triphenylphosphine (80 mg) in 5 ml of triethylamine under argon was added 42 ml of trimethylsilylacetylene. The solution was refluxed for 4 hours and then partitioned between 150 ml of methylene chloride and 50 ml of water. The methylene chloride layer, dried over magnesium sulphate, was evaporated to an oil. This oil was purified by column chromatography on silica gel (10% ethyl acetate:petrolium ether, IR: 2130, 1820, 1762 cm$^{-1}$.

EXAMPLE 4

5(E)-(3-Trimethylsilylpropyn-2-ylidene)-tetrahydro-2-furanone

A 3 neck-flask was equipped with argon gas inlet, outlet and septum. The flask was flushed with argon. A solution of 1.77 gm of 5(E)-iodomethylidenetetrahydro-2-furanone was added to the flask, followed by 109 mg of bis(triphenylphosphine)-palladium (II) chloride and cuprous chloride (106 mg). Trimethylsilylacetylene (1.08 ml) was added and the resulting mixture was stirred at 35° C. for 6 hours. The reaction mixture was diluted with methylene chloride and the solvent evaporated, giving a residue. This residue was extracted with toluene and filtered. The toluene extract was evaporated to an oil which was further purified by column chromatography on silica gel (elution gradient, hexane, 10% ethyl acetate:hexane). This procedure yielded the title compound after recrystallization from hexane, m.p. 51.5°–52° C.; IR: 2130, 1800, 1762 cm$^{-1}$.

Similarly, replacing the 5(E)-iodomethylidenetetrahydro-2-furanone with other compounds of Example 1, the following compounds were prepared:

3-benzyl-3-methyl-5(E)-(3-trimethylsilylprop-2-ynylidene)tetrahydro-2-furanone, IR: 1800, 1663 cm$^{-1}$;

3-benzyl-5(E)-(1-methyl-3-trimethylsilylprop-2-ynylidene)tetrahydro-2-furanone, IR: 1800, 1660 cm$^{-1}$;

3-benzyl-5(E)-(3-trimethylsilylprop-2-ynylidene)-tetrahydro-2-furanone, IR: 2120, 1800, 1660 cm$^{-1}$;

3-butyl-5(E)-3-trimethylsilylprop-2-ynylidene)-tetrahydro-2-furanone, IR: 2130, 1810, 1660 cm$^{-1}$; and 3-isopropyl-5(E)-(3-trimethylsilylprop-2-ynylidene)-tetrahydro-2-furanone, IR: 2980, 2130, 1810, 1660 cm$^{-1}$.

Similarly, replacing the 5(E)-iodomethylidenetetrahydro-2-furanone with the compounds of Example 1 and trimethylsilylacetylene with propyne, there was prepared:

3-benzyl-5(E)-(2-butynylidene)tetrahydro-2-furanone, m.p. 74°–76° C.

Similarly, replacing 5(E)-iodomethylidene tetrahydro-2-furanone with the compounds of Example 1, there were prepared:

3-benzyl-6(E)-(3-trimethylsilylprop-2-ynylidene)-tetrahydro-2-pyrone, IR: 2130, 1780, 1635 cm$^{-1}$; and 6(E)-(3-trimethylsilylprop-2-ynylidene)tetrahydro-2-pyrone, m.p. 76°–78° C., IR: 2120, 1780, 1632 cm$^{-1}$.

EXAMPLE 5

5(E)-(Propy-2-ynylidene)tetrahydro-2-furanone

To a solution of 5(E)-(3-trimethylsilylprop-2-ynylidene)tetrahydro-2-furanone (250 mg, 1.29 mmol) in 5 ml of absolute ethanol under argon at 0° C., was added a solution of silver nitrate (0.879 gm, 5.17 mmol in 7 ml water). A white suspension was formed immediately which was stirred for 30 minutes at 0° C. in the dark. Meanwhile, a solution of 2 gm of potassium cyanide in 20 ml of water was prepared. The reaction mixture was mixed with 5 ml of methylene chloride and poured into the potassium cyanide solution with rapid stirring. The mixture was extracted with methylene chloride (2×25 ml). The methylene chloride layer, dried over sodium sulphate, was evaporated to a solid. The solid was recrystallized from methylene chloride:-hexane (9:1), to give the title compound m.p. 87°–88° C., IR: 3300, 1810, 1660, 2100 cm$^{-1}$.

Proceeding similarly, but replacing 5(E)-(3-trimethylsilylprop-2-ynylidene)tetrahydro-2-furanone by the compounds of Example 4, there was prepared:

3-benzyl-6(E)-(prop-2-ynylidene)tetrahydro-2-pyrone, IR: 2178, 1755, 1636 cm$^{-1}$;

3-benzyl-3-methyl-5(E)-(prop-2-ynylidene)tetrahydro-2-furanone, IR: 3280, 2102, 1795, 1660 cm$^{-1}$;

3-benzyl-5(E)-(1-methyl-prop-2-ynylidene)tetrahydro-2-furanone, IR: 1800, 1665 cm$^{-1}$;

3-isopropyl-5(E)-(prop-2-ynylidene)tetrahydro-2-furanone, IR: 3290, 1805, 1665, 2100 cm$^{-1}$;

3-butyl-5(E)-(prop-2-ynylidene)tetrahydro-2-furanone, IR: 3300, 2100, 1805, 1655 cm$^{-1}$; and 3-benzyl-5(E)-(prop-2-ynylidene)tetrahydro-2-furanone, IR: 3300, 1800, 1600, 2100 cm$^{-1}$.

EXAMPLE 6

| Ingredients | Quantity per tablet, mgs. |
|---|---|
| Active ingredient | 25 |
| corn starch | 20 |
| lactose, spray-dried | 153 |
| magnesium stearate | 2 |

The above ingredients are thoroughly mixed and pressed into single scored tablets.

EXAMPLE 7

| Ingredients | Quantity per tablet, mgs. |
|---|---|
| Active ingredient | 100 |
| lactose, spray-dried | 148 |
| magnesium stearate | 2 |

The above ingredients are mixed and introduced into a hard-shell gelatin capsule.

EXAMPLE 8

An injectable preparation buffered to a pH of 7 is prepared having the following composition:

| Ingredients | |
|---|---|
| Active ingredient | 0.2 g |
| KH$_2$PO$_4$ buffer (0.4 M solution) | 2 ml |
| KOH (1 N) | q.s. to pH 7 |
| water (distilled, sterile) | q.s. to 20 ml |
| (GL-Q) | |

EXAMPLE 9

An injectable preparation buffered to a pH of 7 is prepared having the following composition:

An oral suspension is prepared having the following composition:

| Ingredients | |
|---|---|
| Active ingredient | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

EXAMPLE 10

Inactivation of Human Leukocyte Elastase cl A. Preparation of the enzyme

Following the procedures of Barrett, A. J. (1981), *Methods in Enzymology*, 80C, 581–588, and Engelbrecht, et al., (1982), *J. Physiol. Chem.*, 363, 305–315, fresh human leukocytes were obtained from a healthy donor, frozen and stored at −75° C. until used. Cells were washed in saline, homogenized in the presence of 1M NaCl and 0.1% Brij 35 (Sigma Chemical Co., Cat. No. P-1254). After centrifugation and concentration by dialysis against polyethylene glycol (MW 20,000), the material was chromatographed on Sephacryl S-300 (Pharmacia). Active fractions were combined, concentrated as before, and chromatographed on an affinity gel of bovine lung tyrpsin inhibitor attached to Sepharose CL-4B. Active fractions were combined, concentrated as before to approximately 0.3 micromolar in active elastase, and frozen in 1 ml aliquots at −75° C. until used.

B. Substrate

Methoxysuccinyl-L-alanyl-L-alanyl-L-prolyl-L-valyl-N-m-ethyl-coumarinamide was obtained from Peninsula Laboratories, San Carlos, Calif. Solutions of 1 mM in dimethylsulfoxide were made and kept at 4° C. until use.

C. Inhibitor

3-Benzyl-5(E)-(prop-2-ynylidene)tetrahydro-2-furanone was made to 2 mM in dimethylsulfoxide.

D. Assay Buffer

The buffer consisted of 25 mM N-2-hydroxyethylpiperazine-N-2-ethane sulfonic acid, 1M sodium chloride, 0.1% w/v Brij 35, pH 7.8.

E. Procedure

A Perkin-Elmer Model 650-40 fluorescence spectrophotometer was set up as follows: ratio mode, excitation 370 nm, emission 460 nm, full scale output 1, 5, or 10 units, cell compartment thermostated at 25° C. To 2.0 ml of assay buffer in a fluorescence cuvette was added 4 microliters substrate and 20 microliters enzyme, with mixing. The change in fluorescence was recorded on a strip chart recorder to measure the initial, uninhibited rate, typically 0.8 units per minute. After approximately two minutes of such recording, inhibitor (between 0.5 and microliters) was added with mixing, and recording continued.

The enzyme was inactivated in a time and concentration dependent manner with a maximum inactivation rate of 0.09 s$^{-1}$ and an inhibitor concentration required for half-maximal rate of 4.1 micromolar.

The irreversibility of this inactivation was shown as follows: to 0.8 ml of the assay buffer at 25° C. containing 0.24 nanomoles of HL elastase was added 4 microliters of the 2 mM inhibitor solution. At various times (0 to 15 minutes), 20 microliter aliquots were withdrawn and assayed for enzyme activity as described above. After 17 minutes, the enzyme solution was rapidly chromatographed on Sephadex G-50 (Pharmacia) in the same buffer. The enzyme fractions were assayed for activity as above.

What is claimed is:

1. A compound of the formula

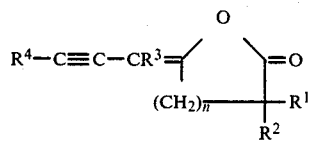

wherein n is 1; $R^1$ is hydrogen or lower alkyl; $R^2$ is hydrogen, lower alkyl, or phenyl lower alkyl; $R^3$ is hydrogen or lower alkyl; and $R^4$ is hydrogen, lower alkyl, or trialkylsilyl; excluding those compounds wherein $R^1$ and $R^2$ are hydrogen and $R^4$ is ethyl, propyl or butyl.

2. A compound of claim 1 which is 3-benzyl-5(E)-(prop-2-ynylidene)tetrahydro-2-furanone.

3. A compound of claim 1 which is 3-n-butyl-5(E)-(prop-2-ynylidene)tetrahydro-2-furanone.

4. A compound of claim 1 which is 3-methyl-3-benzyl-5(E)-(prop-2-ynylidene)tetrahydro-2-furanone.

5. A compound of claim 1 which is 3-benzyl-5(E)-(2-butynylidine)tetrahydro-2-furanone.

6. A compound of claim 1 which is 5(E)-(3-trimethylsilylprop-2-ynylidene)tetrahydro-2-furanone.

7. A pharmaceutically acceptable composition which comprises a compound according to claim 1 and a pharmaceutically acceptable excipient.

8. A method for inhibiting protease which method comprises administering to a mammal an amount of a compound of formula I of claim 1 which effectively inhibits proteases either alone or in admixture with a pharmaceutically acceptable excipient.

* * * * *